(12) United States Patent
Terranova et al.

(10) Patent No.: US 7,498,461 B2
(45) Date of Patent: Mar. 3, 2009

(54) METHOD FOR THE PREPARATION OF 6-[3-(1-ADAMANTYL)-4-METHOXYPHENYL]-2-NAPHTHOIC ACID

(75) Inventors: Eric Terranova, Magagnosc (FR); Jean-Claude Pascal, Nice (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 11/905,955

(22) Filed: Oct. 5, 2007

(65) Prior Publication Data

US 2008/0091045 A1 Apr. 17, 2008

Related U.S. Application Data

(63) Continuation of application No. PCT/EP2006/003790, filed on Apr. 6, 2006.

(60) Provisional application No. 60/778,112, filed on Mar. 1, 2006.

(30) Foreign Application Priority Data

Apr. 8, 2005 (FR) .................................. 05 03522

(51) Int. Cl.
*C07C 63/34* (2006.01)
(52) U.S. Cl. ...................................... 562/467
(58) Field of Classification Search ............... None
See application file for complete search history.

(56) References Cited

U.S. PATENT DOCUMENTS

2006/0229465 A1* 10/2006 Castaldi et al. ............... 560/56

FOREIGN PATENT DOCUMENTS

CN             1696100         * 11/2005

OTHER PUBLICATIONS

Miyaura et al, Chemical Reviews. Palladium-Catalyzed Cross-Coupling Reactions of Organoboron Compounds, 1995, 85, pp. 2457-2483.*

* cited by examiner

*Primary Examiner*—Paul A Zucker
(74) *Attorney, Agent, or Firm*—Buchanan, Ingersoll & Rooney, P.C.

(57) ABSTRACT

A novel method for preparing 6-[3-(1-adamantyl)-4-methoxyphenyl]-2-naphthoic acid includes a Suzuki reaction between 3-adamantyl-4-methoxyphenylboronic acid of formula (II):

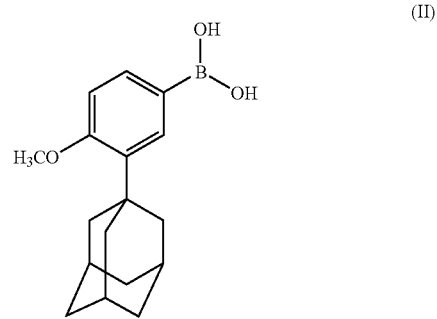

and 6-bromo-2-naphthoic acid of formula (III):

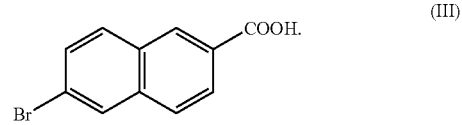

11 Claims, No Drawings

METHOD FOR THE PREPARATION OF 6-[3-(1-ADAMANTYL)-4-METHOXYPHENYL]-2-NAPHTHOIC ACID

CROSS-REFERENCE TO PRIORITY/PCT/PROVISIONAL APPLICATIONS

This application claims priority under 35 U.S.C. § 119 of FR 05/03522, filed Apr. 8, 2005, and of Provisional Application No. 60/778,112, filed Mar. 1, 2006, and is a continuation of PCT/EP 2006/003790 filed Apr. 6, 2006 and designating the United States, published in the English language as WO 2006/108717 A2 on Oct. 19, 2005, each hereby expressly incorporated by reference in its entirety and each assigned to the assignee hereof.

BACKGROUND OF THE INVENTION

1. Technical Field of the Invention

The present invention relates to a novel method for the preparation of 6-[3-(1-adamantyl)-4-methoxyphenyl]-2naphthoic acid of formula (I):

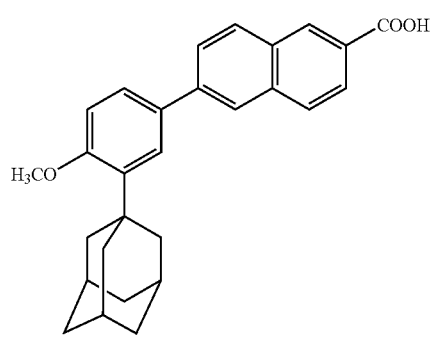

(I)

a retinoid local anti-acne agent, useful when formulated into pharmaceutical compositions, in particular for the treatment of certain types of acne.

2. Description of Background and/or Related and/or Prior Art

The compound of formula (I) is described in particular in EP-0,199,636. EP-0,199,636 describes the preparation of this compound according to the following Scheme 1:

Scheme 1:

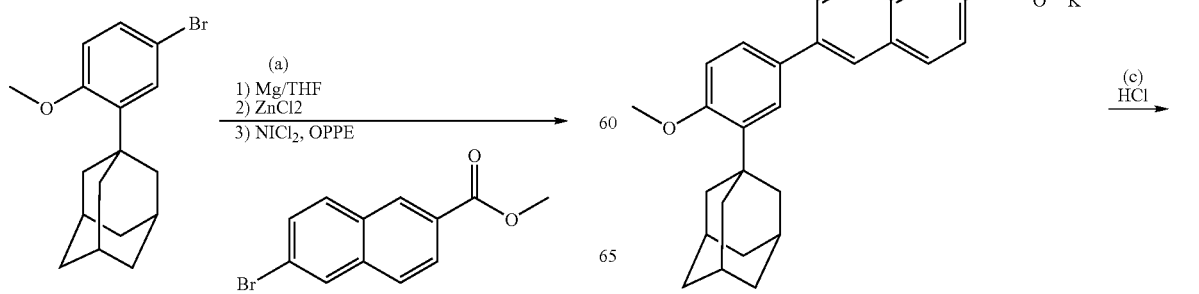

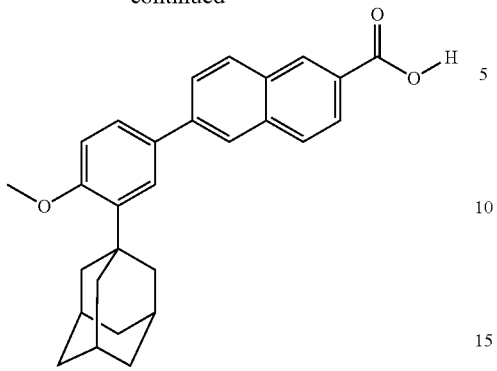

In this method, 2-(1-adamantyl)-4-bromoanisole is converted, in a first step (a), to its organomagnesium compound, and then to its organozinc compound by the action of zinc chloride (ZnCl$_2$), and is then coupled with methyl 6-bromonaphthoate. This reaction is catalyzed by a transition metal (palladium or nickel) or one of its complexes with various phosphines. The synthesis of 6-[3-(1-adamantyl)-4-methoxyphenyl]-2naphthoic acid of formula (I), as described in EP-0,199,636 (Scheme 1), is therefore carried out in three steps with a yield of 63%, from 2-adamantyl-4-bromoanisole.

One of the disadvantages of this reaction is the formation of impurities. One of these impurities results from the reaction of the organozinc compound generated "in situ" with 2-adamantyl-4-bromoanisole to give 3,3'-di(1-adamantyl)-4,4'-dimethoxy-1,1'-biphenyl having the following structure:

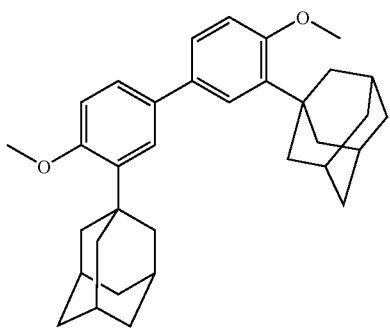

Another impurity also forms via the transfer of the zinc compound of 2-(1-adamantyl)-4-bromoanisole to methyl 6-bromonaphthoate and the reaction of this novel zinc compound with methyl 6-bromonaphthoate to give the dimerization product having the structure:

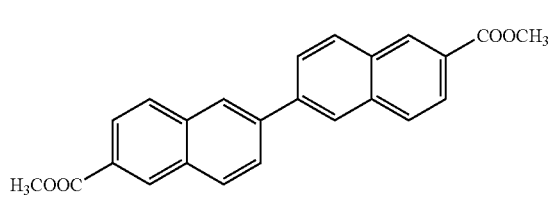

This product leads, after saponification (step (b)) and acidification (step (c)), to the following impurity:

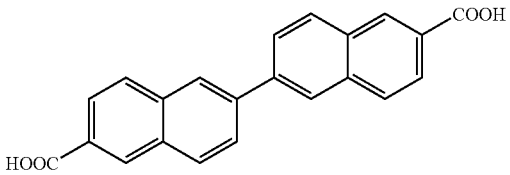

A third impurity forms during the hydrolysis of the reaction medium. Indeed, during this hydrolysis, the unreacted organozinc compound of 2-(1-adamantyl)-4-bromoanisole generates the impurity having the following structure:

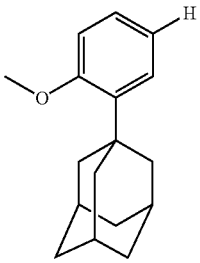

At an industrial stage, these impurities are difficult to remove from the finished product and most often require reprocessing by recrystallization.

Furthermore, certain catalysts such as [1,2-bis(diphenylphosphino)ethane]nickel chloride (NiCl$_2$(dppe)) must be prepared separately, adding a step to this method.

During the coupling reaction in step (a), the acid functional group is protected in methyl ester form. This acid functional group should be regenerated. Thus, in a second step (b), methyl 6-[3-(1-adamantyl)-4-methoxyphenyl]-2-naphthoate is saponified by treating with a base such as sodium hydroxide (NaOH) or potassium hydroxide (KOH) under reflux in an alcohol such as methanol.

By acidifying the reaction medium with hydrochloric acid, 6-[3-(1-adamantyl)-4-methoxyphenyl]-2-naphthoic acid is obtained in a third step (c). It should also be noted that in this method, the methyl ester of 6-bromonaphthoic acid should be prepared in one step from the corresponding acid. It can therefore be seen that the prior art method is complex and is not entirely satisfactory.

SUMMARY OF THE INVENTION

The present invention thus features a method for preparing 6-[3-(1-adamantyl)-4-methoxyphenyl]-2-naphthoic acid, which is far simpler and more economical. The method according to the invention is more suited to industrial application, more particularly in terms of cost and compliance with Good Manufacturing Practices. This invention provides a novel method for preparing compound (I) which does not require in the final stage deprotection of the acid functional group, avoiding the formation of the impurities indicated above and making it possible to reduce the number of synthesis steps.

In this respect, the present invention features a method for preparing 6-[3-(1-adamantyl)-4-methoxyphenyl]-2-naphthoic acid of formula (I):

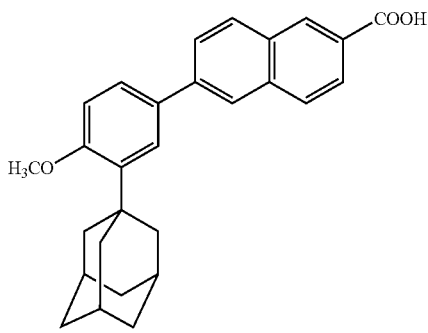

by a single step Suzuki reaction from 3-adamantyl-4-methoxyphenylboronic acid of formula (II):

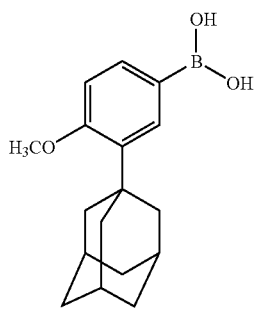

and 6-bromo-2-naphthoic acid of formula (III):

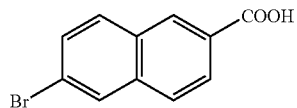

This invention also features the use of the compound (II), on the one hand, and the use of the compound (III), on the other hand, for the preparation of the compound of formula (I).

According to the method of the invention, it is therefore possible to couple in a single step the (1-adamantyl)phenyl part and the naphthyl part of 6-[3-(1-adamantyl)-4-methoxyphenyl]-2-naphthoic acid.

The preparation of 6-[3-(1-adamantyl)-4-methoxyphenyl]-2-naphthoic acid, according to the method of the invention, is illustrated in Scheme 2 below:

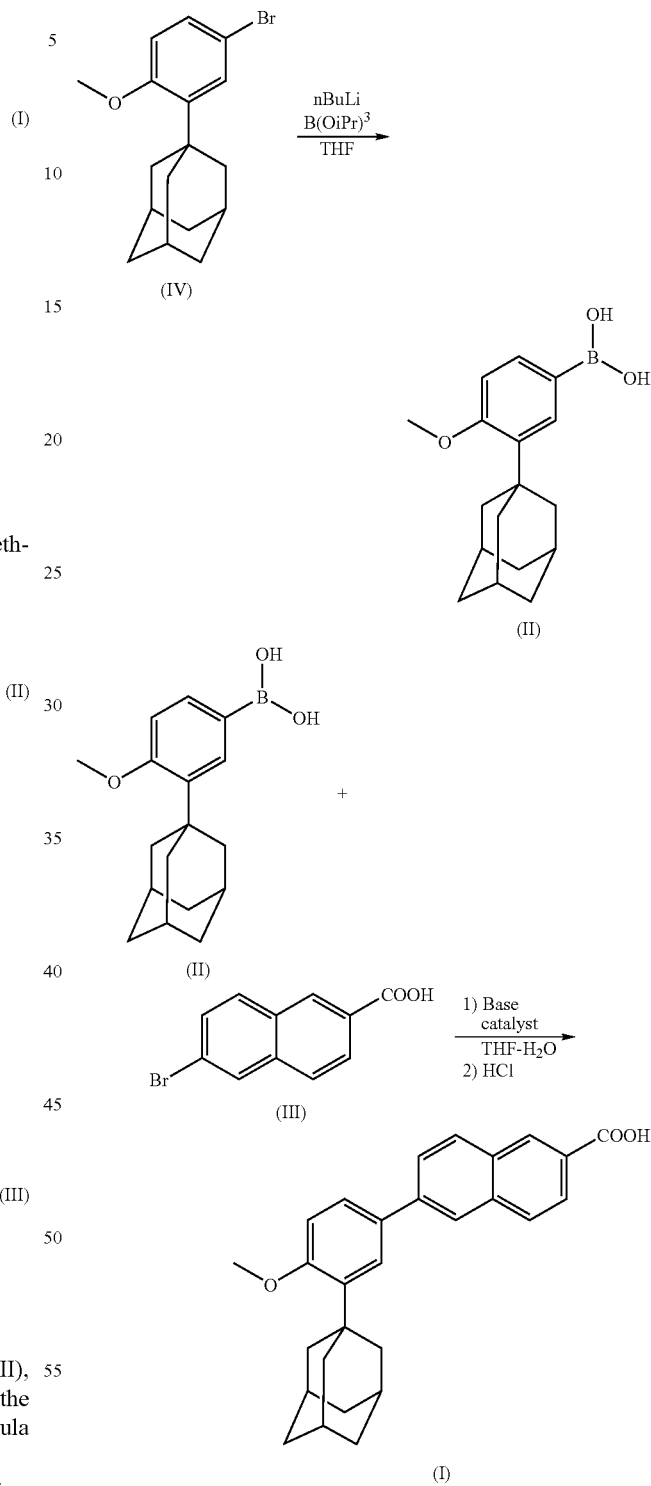

The preparation of 6-[3-(1-adamantyl)-4-methoxyphenyl]-2-naphthoic acid (I) is carried out by the Suzuki reaction from 3-adamantyl-4-methoxyphenylboronic acid (II) (prepared in particular according to a method similar to that described in WO 02/072009 A2 and WO 03/011808 A1) and the commercially available 6-bromo-2-naphthoic acid (III).

The preparation of 6-[3-(1-adamantyl)-4-methoxyphenyl]-2-naphthoic acid of formula (I) as described by this novel method according to Scheme 2 is carried out in two steps from 2-(1-adamantyl)-4-bromoanisole (IV) (prepared for example according to EP-0,199,636), with a yield which is much higher than that obtained with the prior art method. As shown by the example which follows, the yield of the method according to the invention may be on the order of 95% or higher.

According to the invention, the Suzuki reaction is carried out by coupling from compounds (II) and (III) in the presence of a palladium catalyst and a base, in a polar solvent, followed by an acid treatment.

Typically, the Suzuki reaction may be carried out in the presence of a palladium catalyst such as palladium(II) acetate, tetrakis(triphenylphosphine)palladium (0), palladium on activated charcoal or dichloro[1,1'-bis(diphenylphosphino)ferrocene]palladium(II), in an aprotic polar solvent (for example acetonitrile, N,N-dimethylformamide, dimethoxyethane or tetrahydrofuran) or a protic polar solvent (for example n-propanol, i-propanol) or a mixture of these solvents with water. The volume of solvent used will be from 7 and 13 times the quantity of 6-bromo-2-naphthoic acid (III) used and the volume of water used will be from 7 and 13 times the quantity of 6-bromo-2-naphthoic acid (III) used.

Advantageously, the palladium catalyst may contain a ligand selected from: a triphenylphosphine, a tri-o-tolylphosphine, a tri-m-tolylphosphine or a tri-p-tolylphosphine. The catalysts particularly preferred are palladium(II) acetate and palladium on carbon which make it possible to obtain particularly fast reaction kinetics. Palladium(II) acetate may be advantageously used in combination with a 2-(dicyclohexylphosphino)biphenyl type ligand (J. P. Wolfe et al., *J. Am. Chem. Soc.*, 1999, 121, 9550-9561).

These catalysts may also be encapsulated, such as for example the Pd EnCat™ type catalysts. The reaction is generally carried out in the presence of an inorganic base such as potassium carbonate, sodium carbonate, caesium carbonate, sodium hydroxide or potassium hydroxide or in the presence of a tertiary amine such as triethylamine or diisopropylethylamine. The particularly preferred bases are potassium carbonate, potassium hydroxide and diisopropylethylamine.

The Suzuki reaction is preferably carried out under an inert atmosphere, for example under an argon or nitrogen atmosphere. The reaction mixture is advantageously heated at a temperature in the range from 60° to 110° C., for 30 minutes to 24 hours. A treatment in an acidic medium, for example in the presence of HCl, is carried out. It will be noted that, according to the conditions used in Examples 1 and 2, the kinetics of the reaction is very rapid and is complete within two hours. One skilled in the art will be able to modify these conditions, in particular by applying the variants of the Suzuki reaction which are described in the literature (N. Miyaura & A. Suzuki, *Chem. Rev.*, 1995, 95, 2457-2483; A. Suzuki, *J. Organomet. Chem.*, 1999, 576, 147-168). The method according to the invention is therefore simple and economical and makes it possible to directly obtain compound (I) with a high yield, close to quantitative.

This novel method also makes it possible to obtain 6-[3-(1-adamantyl)-4-methoxyphenyl]-2-naphthoic acid with a high degree of purity in which the impurities obtained in the prior art method are completely absent.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1 a) Preparation of 3-adamantyl-4-methoxyphenylboronic acid (II)

100 g (0.311 mol) of 2-(1-adamantyl)-4-bromoanisole (IV) and 500 ml of THF are introduced, under nitrogen, into a 2 L three-necked reactor. The reaction medium is cooled to −75° C. 137 ml (0.342 mol) of a 2.5 M nBuLi solution are added. After stirring for 1 h at −70° C., 80 ml (0.342 mol) of triisopropyl borate are added. After returning to room temperature, the reaction mixture is hydrolyzed with 1 liter of 1.2 N HCl. The aqueous phase is extracted with ethyl acetate and the combined organic phases are washed with 1 liter of saturated NaCl, and then with 1 liter of water. The organic phases are dried over sodium sulfate and the solvents are evaporated. 88.37 g of a white solid are obtained, which solid is reimpasted in 440 mL of heptane. After filtration, the precipitate obtained is rinsed with heptane, and then dried under reduced pressure at 35° C. until a constant weight is obtained. 84.4 g of 3-adamantyl-4-methoxyphenylboronic acid are obtained in the form of a white solid—(yield=94.8%; m.p.=263° C.).

$^1$H NMR (CDCl$_3$): δ:1.77 (s; 6H); 2.10 (m; 3H); 2.20 (s; 6H); 3.91 (s; 3H); 7.00 (d; 1H; J$_1$=8.0 Hz); 8.05 (dxd; 1H; J$_2$=1.5 Hz and J$_1$=8.0 Hz); 8.15 (d; 1H, J$_2$=1.5 Hz)

b) Preparation of 6-[3-(1-adamantyl)-4-methoxyphenyl]-2-naphthoic acid (I)

20 mL of tetrahydrofuran (12 vol.), 2 g (7 mmol) of 3-adamantyl-4methoxyphenylboronic acid (II), 1.65 g (6.6 mmol) of 6-bromo-2-naphthoic acid (III) and 20 mL of a 2 M aqueous potassium carbonate solution are introduced into a round-bottomed flask equipped with stirring and under a nitrogen stream. 15 mg (1%) of palladium acetate and 46 mg (2%) of 2-(dicyclohexylphosphino)biphenyl are then introduced. The medium is heated under reflux for 2 hours. Kinetic monitoring by HPLC indicates that the % of 6-[3-(1-adamantyl)-4-methoxyphenyl]-2-naphthoic acid formed is 94% after one hour and 98% after 2 h.

After returning to room temperature, the catalyst is filtered on a cartridge, and then slowly poured over 30 ml of a 1 N aqueous hydrochloric acid solution.

The medium is maintained under stirring for one hour. The precipitate is filtered, washed with water and then dried under reduced pressure. 2.68 g of 6-[3-(1-adamantyl)-4-methoxyphenyl]-2-naphthoic acid are obtained in the form of a white solid whose purity, determined by HPLC, is 99.9% (yield=94.8%; m.p.=321° C.).

The following melting points (m.p.) exist in the literature: m.p.=319°-322° C. (B. Charpentier et al., *J. Med. Chem.*, 1995, 38, 4993-5006)

and m.p.=325°-327° C. (EP 0 199 636).

EXAMPLE 2 a) Preparation of 6-[3-(1-adamantyl)-4-methoxyphenyl]-2-naphthoic acid (I)

80 g (0.319 mol) of 6-bromo-2-naphthoic acid, 95.7 g (0.335 mol, 1.05 eq.) of 3-adamantyl-4-methoxyphenyl-boronic acid, 0.8 g of 5% palladium on carbon (50% wet, Degussa type E105CA/W) and 800 ml of tetrahydrofuran (10 vol.) are introduced into a 4 liter reactor. The medium is heated to 55° C. 85 g (1.05 mol, 3.3 eq) of potassium hydroxide at 85% are dissolved in 240 ml of water (3 vol.).

The solution obtained is poured over the reaction medium. The addition is exothermic. The reaction medium reaches the reflux temperature. The reflux is maintained for about 2 hours.

The reaction medium is filtered at about 35-40° C. on a cartridge and rinsed with 400 ml of a THF/water mixture (1/1).

The medium is cooled to 20° C. and 100 ml of HCl at 35% in 600 ml of water are added. 6-[3-(1-adamantyl)-4-methoxyphenyl]-2-naphthoic acid precipitates. It is filtered and washed with 4 liters of water. The pH of the washings is about 6-7. The product is dried under vacuum at 100° C. for 24 hours.

131 g of 6-[3-(1-adamantyl)-4-methoxyphenyl]-2-naphthoic acid are obtained (crude yield=99%).

This crude material is dissolved in 15 to 22 volumes of THF under reflux. After filtration in the hot state, 15 to 22 volumes of heptane are added and the medium is cooled to about 5° C. for 1 to 2 hours.

The 6-[3-(1-adamantyl)-4-methoxyphenyl]-2-naphthoic acid is filtered on sintered glass and it is rinsed with 1 to 2 volumes of heptane.

108 g of 6-[3-(1-adamantyl)-4-methoxyphenyl]-2-naphthoic acid are obtained in the form of a white solid whose purity, determined by HPLC, is 99.9% (yield=82%; m.p.=320-322° C.).

EXAMPLE 3 a) Preparation of 6-[3-(1-adamantyl)-4-methoxyphenyl]-2-naphthoic acid (I)

20 ml (12 vol.) of tetrahydrofuran, 2 g (7 mmol) of 3-adamantyl-4methoxyphenylboronic acid (II), 1.65 g (6.6 mmol) of 6-bromo-2-naphthoic acid (III) and 20 mL of a 2 M aqueous potassium carbonate solution are introduced into a round-bottomed flask equipped with stirring and under a nitrogen stream. 0.7 g (5%) of 10% palladium on carbon (50% wet; Heraeus type K-0218) is then introduced.

The medium is heated under reflux for 8 hours. The catalyst is filtered on a cartridge, and then slowly poured over 30 ml of a 1 N aqueous hydrochloric acid solution.

The medium is kept stirring for one hour. The precipitate is filtered, washed with water and then dried under reduced pressure. 2.06 g of 6-[3-(1-adamantyl)-4-methoxyphenyl]-2-naphthoic acid are obtained in the form of a white solid whose purity, determined by HPLC, is 99.9% (yield=79%; m.p.=321° C.).

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for preparing 6-[3-(1-adamantyl)-4-methoxyphenyl]-2-naphthoic acid of formula (I):

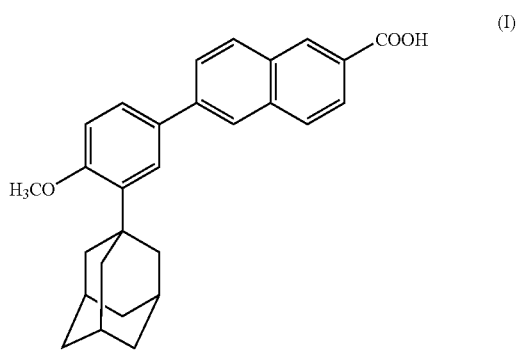

comprising coupling 3-adamantyl-4-methoxyphenylboronic acid of formula (II):

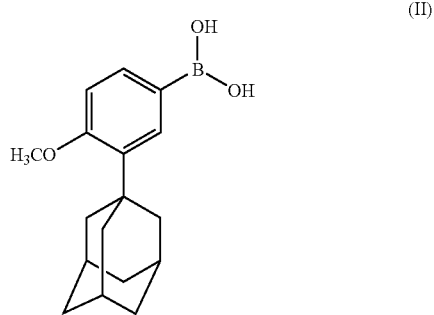

and 6-bromo-2-naphthoic acid of formula (III):

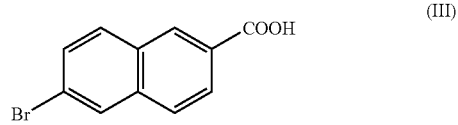

according to a Suzuki reaction.

2. The method as defined by claim 1, wherein said Suzuki reaction is carried out by coupling from compounds (II) and (III) in the presence of a palladium catalyst and a base, in a polar solvent, followed by an acid treatment.

3. The method as defined by claim 2, wherein the catalyst comprises palladium(II) acetate, palladium on activated charcoal, dichloro[1,1'-bis(diphenylphosphino)ferrocene]palladium(II), a palladium complex containing a phosphine ligand or tetrakis(triphenylphosphine)palladium.

4. The method as defined by claim 3, the catalyst comprising a phosphine ligand selected from the group consisting of 2-(dicyclohexylphosphino)biphenyl, triphenylphosphine, tri-o-tolylphosphine, tri-m-tolylphosphine and tri-p-tolylphosphine.

5. The method as defined by claim 3, wherein the catalyst comprises palladium(II) acetate or palladium on activated charcoal.

6. The method as defined by claim 5, wherein the catalyst comprises palladium(II) acetate in the presence of the ligand 2-(dicyclohexylphosphino)biphenyl.

7. The method as defined by claim 2, wherein the base comprises an inorganic base selected from the group consisting of potassium carbonate, sodium carbonate, caesium carbonate, sodium hydroxide, potassium hydroxide, triethylamine and diisopropylethylamine.

8. The method as defined by claim 2, wherein the polar solvent is selected from the group consisting of acetonitrile, N,N-dimethylformamide, dimethoxyethane, tetrahydrofuran, n-propanol, i-propanol and a mixture of such solvents with water.

9. The method as defined by claim 2, wherein the coupling is carried out at a temperature ranging from 60 to 110° C., for 30 minutes to 24 hours, under an inert argon or nitrogen atmosphere.

10. The method as defined by claim 2, wherein the acid treatment is carried out with hydrochloric acid.

11. The method as defined by claim 2, wherein the volume of solvent is from 7 and 13 times the quantity of 6-bromo-2-naphthoic acid (III) and the volume of water is from 7 and 13 times the quantity of 6-bromo-2-naphthoic acid (III).

* * * * *